United States Patent [19]
Schick et al.

[11] Patent Number: 5,196,169
[45] Date of Patent: Mar. 23, 1993

[54] METHOD AND SYSTEM FOR DETERMINING FREE FATTY ACID CONTENT

[75] Inventors: Karl G. Schick; Paul M. Karges, both of Milwaukee; Gary A. Lang, Brookfield; David A. Uhen, Palmyra, all of Wis.

[73] Assignee: Eppendorf North America, Inc., Madison, Wis.

[21] Appl. No.: 771,318

[22] Filed: Oct. 2, 1991

Related U.S. Application Data

[63] Continuation of Ser. No. 666,546, Mar. 7, 1991, abandoned, which is a continuation of Ser. No. 582,139, Sep. 13, 1990, abandoned, which is a continuation of Ser. No. 436,976, Nov. 16, 1989, abandoned, which is a continuation of Ser. No. 127,626, Dec. 1, 1987, abandoned, which is a continuation of Ser. No. 902,646, Sep. 2, 1986, abandoned.

[51] Int. Cl.$^5$ .................. G01N 33/03; G01N 35/08
[52] U.S. Cl. .................... 422/81; 422/68.1; 422/82.05; 436/23; 436/52; 436/60; 436/61; 436/129
[58] Field of Search .......... 436/20, 23, 52, 60, 436/61, 129; 422/61, 68.1, 81, 82.05

[56] References Cited

U.S. PATENT DOCUMENTS

| | | | |
|---|---|---|---|
| 3,488,154 | 1/1970 | Hronas | 422/81 X |
| 3,615,226 | 10/1971 | Apter | 436/20 |
| 4,013,413 | 3/1977 | Stewart et al. | 436/52 X |
| 4,022,575 | 5/1977 | Hansen et al. | 436/52 |
| 4,338,280 | 7/1982 | Ambers et al. | 422/68 |
| 4,384,206 | 5/1983 | Bjarno | 436/129 X |

FOREIGN PATENT DOCUMENTS

| | | | |
|---|---|---|---|
| 4015238 | 4/1974 | Japan | 436/20 |
| 805170 | 2/1981 | U.S.S.R. | 436/20 |

OTHER PUBLICATIONS

Ross, et al., "A New Type, Rapid Method for Determination of Fat in Potato Chips," *Potato Chipper*, Jul. 1961, pp. 1-4.
Koch, et al., "Fatty Acid Analysis by Tracer Methods," J. Radioanal. Chem., 35(1), pp. 197-206.
Beardsley, "The Separation and Determination of Fatty Acids by Isotopic Dilution and Radiogas-Liquid Chromatography," Talanta, 28(6), pp. 405-407.

*Primary Examiner*—Jill A. Johnston
*Attorney, Agent, or Firm*—Marshall, O'Toole, Gerstein, Murray & Bicknell

[57] ABSTRACT

The free fatty acid content of an edible oil is measured by a system including a supply of a carrier solution containing an organic solvent for dissolving the oil and a color indicating reagent and an oil sample supply connected to a flow-through colorimetric detector via a sample injection valve. The sample injection valve is movable between a load position wherein a sample stream of the oil is routed to a sample waste collector via a sample loop and a stream of the carrier solution passes through the detector via a carrier solution conduit and a measure position wherein a slug of the oil in the sample loop is introduced into the carrier solution conduit and mixed with the carrier solution prior to passing through the detector. The free fatty acid in the oil reacts with the color indicating reagent in the carrier solution to produce a color of an intensity indicative of the free fatty acid content which is measured by the detector. The system also includes a selector valve manifold including up to three different calibration solutions which can be selectively introduced.

17 Claims, 2 Drawing Sheets

5,196,169

METHOD AND SYSTEM FOR DETERMINING FREE FATTY ACID CONTENT

CROSS REFERENCE TO RELATED APPLICATIONS

This application is a continuation of U.S. application 07/666,546 filed Mar. 7, 1991, abandoned, which is a continuation of U.S. application Ser. No. 07/582,139 filed Sep. 13, 1990, abandoned, which is continuation of U.S. application Ser. No. 07/436,976, filed Nov. 16, 1989, abandoned, which is a continuation of U.S. application Ser. No. 07/127,626, filed Dec. 1, 1987, abandoned, which is a continuation of U.S. application Ser. No. 06/902,646 filed Sep. 2, 1986, abandoned.

BACKGROUND OF THE INVENTION

This invention relates to systems and methods for determining the free fatty acid content in oils, particularly edible oils.

Crude edible oils, such as soybean oil, cottonseed oil, corn oil, fish oil and the like, frequently contain undesirable amounts of free fatty acids which affect their quality. Various techniques are employed to remove free fatty acids and other contaminants. In one technique commonly used, a base is added to the oil to neutralize excessive amounts of free fatty acids. The free fatty acid content for many edible oils should be less than 0.05% and preferably in the range of 0.02 to 0.03%.

A system capable of measuring the free fatty acid content of oils during the refining process is highly desirable for a closer process control which can result in high yields, tighter product specification and an increase in the effectiveness of a subsequent bleaching step. A system capable of continuously producing an output signal representative of the free fatty acid content on a continuous basis is particularly desirable because it can be conveniently incorporated into completely automated process controls.

Conventional detectors employing an electrode type sensor usually cannot be conveniently used to determine the concentration of a component in a non-aqueous medium without incorporating complex auxiliary circuitry or other equipment.

SUMMARY OF THE INVENTION

An object of the invention is to provide a simple, colorimetric system and method for continuously analyzing an oil for the free fatty acid content.

Another object of the invention is to provide such a system and method having the capability of producing highly accurate measurements under a relatively wide range of ambient temperature conditions.

A further object of the invention is to provide such a system and method which can be fully automated.

A still further object of the invention is to provide such a system which employs a pressurized reservoir as the means for supplying a continuous stream of the carrier solution and yet is not subject to significant outgassing or gas bubble formation.

A yet further object of the invention is to provide an automated system and method for analyzing the free fatty acid content of edible oils including a colorimetric detector and the capability of introducing calibration solutions at programmable intervals and generating an updated calibration curve for the detector.

Other objects, aspects and advantages of the invention will become apparent to those skilled in the art upon reviewing the following detailed description, the drawing and the appended claims.

The invention provides a system and method for analyzing an oil to determine free fatty acid content. The system includes means for supplying a continuous sample stream of the oil to be analyzed, means for supplying a continuous stream of a carrier solution containing a solvent for dissolving the oil sample and a color indicating reagent, a flow-through colorimetric detector, a sample loop or conduit means, and a sample injection valve which is movable between a load position wherein the oil sample stream is routed to waste through the sample loop and the carrier solution stream is routed through the detector and a measure position where the sample stream is routed directly to waste and the carrier solution stream is routed to the detector via the sample loop so that an oil sample in the sample loop is mixed with the carrier solution prior to passing through the detector. The color indicating reagent in the carrier solution reacts with the free fatty acid in the oil to produce a color change, the intensity of which is measured by the detector which produces a signal representative of the free fatty acid content. The analyzing system also includes means for heating the oil sample and carrier solution streams and maintaining them at a temperature above a level where the components of the oil tends to separate and means for regulating liquid flow through the detector.

In one embodiment, a computer operates the sample injection valve between the load and measure positions at programmable intervals.

In one embodiment, liquid flow through the detector is regulated by a flow restrictor coil connected to the detector outlet and this coil is maintained at a predetermined, substantially constant temperature.

In one embodiment, mixing of the oil in carrier solution is enhanced by a diffusion coil located between the sample injection valve and the detector.

In one embodiment, separate supplies of calibration solutions containing known concentrations of a fatty acid are provided. The sample injection valve and a selector valve manifold including valves or a controlling flow of the sample and calibration solutions are operated at programmable intervals by the computer which generates an updated calibration curve for the detector.

In one embodiment, the carrier solution is pressurized with a gas, such as air, and the carrier solution is isolated from the pressurizing gas by one or more layers of discrete, bubble-like objects floating on the surface of the carrier solution.

DESCRIPTION OF THE PREFERRED EMBODIMENTS

The analyzing system and method of the invention can be used to measure the free fatty acid content of a wide variety of hydrocarbon oils. The system and method can be used for a wide range of applications, such as for an on-line analysis of a process stream or analysis of an oil used in commercial fryers for free fatty acid content. The invention is particularly adaptable for analyzing edible oils, such as soybean oil, cottonseed oil, corn oil, fish oil, etc. and will be described in connection with an on-line analysis of a process stream for such an oil.

Figure 1:
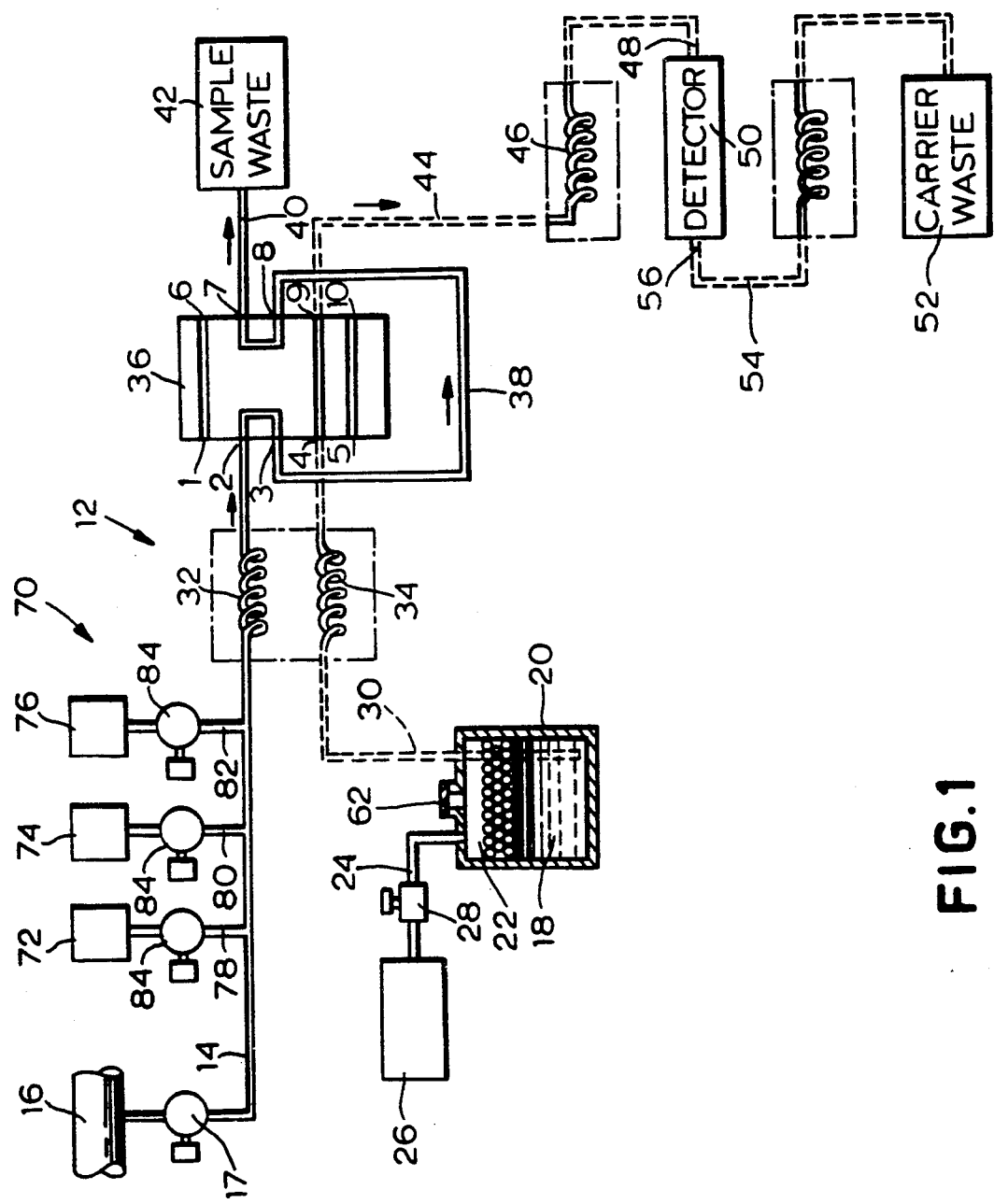
FIG. 1 is a schematic diagram of the analyzing system of the invention shown with the sample injection valve in the load position.

Referring to FIG. 1, the analyzing system 12 includes a sample supply conduit 14 connected to a process line 16 carrying the edible oil to be analyzed. Pressure in the process delivers a continuous stream of the oil into the system through a two-way, pneumatically-operated valve 17 connected to the supply conduit 14.

A carrier solution 18 is contained in a reservoir 20. The carrier solution 18 includes an organic solvent capable of dissolving substantially all the components in the oil, particularly the free fatty acids (e.g., oleic acid), and a color indicating reagent capable of reacting with free fatty acids to produce a measurable color change, the intensity of which indicates the concentration of free fatty acids.

The carrier solution 18 is pressurized with a gas 22, such as air, supplied through a conduit 24 from a suitable source 26, such as a small compressor, and regulated to a desired pressure by a regulator 28 in the conduit 24. The pressurized carrier solution reservoir 20 delivers a continuous stream of the carrier solution 18 through a carrier solution supply conduit 30.

The oil sample and carrier solution streams are preheated to a temperature above the level where components in the oil tend to settle out or separate. This can be accomplished by passing each through respective preheating coils 32 and 34 including a length of coiled tubing wrapped with a thermostaticaly-controlled electric blanket (not shown). This heating blanket maintains the preheating coils 32 and 34 at a substantial constant temperature (e.g., about 70° C.).

The oil supply conduit 14 and the carrier solution supply conduit 30 are connected to a sample injection valve, which in the illustrated the preferred embodiment illustrated is a conventional, pneumatically-operated, slider type valve 36 (e.g., CP Valve marketed by Bendix Corporation). Other suitable type valves can be used, such as a rotary valve.

When the slider valve 36 is in the load position as illustrated in FIG. 1, the oil sample stream enters the valve 36 through port 2, exits the valve 36 through port 3, passes through an external sample conduit or loop 38, reenters the valve 36 through port 8, exits again through port 7 and passes through a sample waste conduit 40 into a sample waste receptacle 42. At the same time, the carrier solution stream enters the valve 36 through port 4, exits the valve 36 through port 9, passes through a carrier solution conduit 44 to a diffusion coil 46 including a length of coiled tubing wrapped with a thermostatically-controlled, electric heating blanket (not shown). This heating blanket maintains the diffusion coil 46 at a substantially constant temperature (e.g., about 70° C.).

The carrier solution conduit 44 is connected to the inlet 48 of a conventional, dual beam, flow-through type colorimetric detector 50 capable of producing an electrical signal representative of the free fatty acid content of a liquid flowing therethrough in response to the color intensity of that liquid (e.g., FIA-LITE 600 marketed by FIAtron Systems, Inc.). The carrier solution stream passing through the detector 50 is routed to a carrier waste receptacle 52 by a carrier waste conduit 54 connected to the outlet 56 of the detector 50. The flow rate of this liquid is controlled by a flow restrictor coil 58 including a length of coiled tubing wrapped with a thermostatically-controlled electric heating blanket (not shown). This heating blanket maintains the flow restrictor coil at a substantially constant temperature (e.g., about 70° C.).

Figure 2:
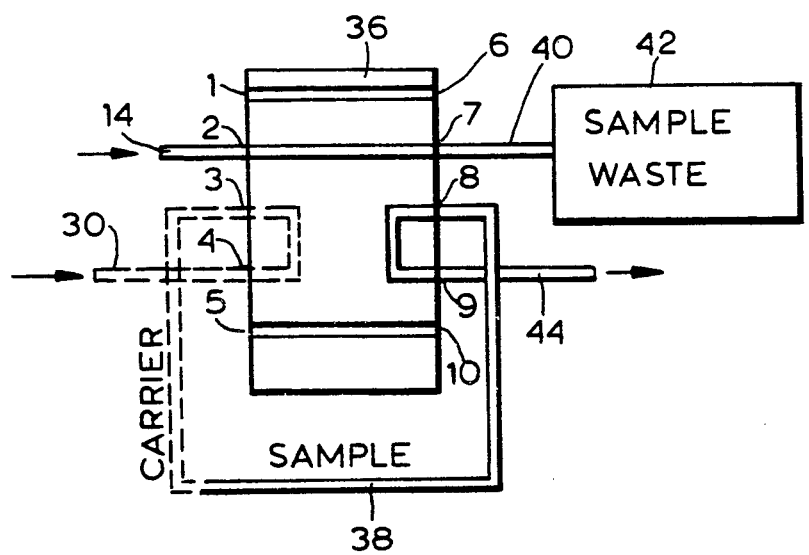
FIG. 2 is a schematic diagram of the sample injection valve in the measure position.

When the slider valve 36 is moved to a measure position illustrated in FIG. 2, the oil sample stream enters the valve 36 through port 2, exits the valve 36 through port 7 and passes directly to the sample waste receptacle 42. At the same time, the carrier solution stream enters the valve 36 through port 4, exits the valve through port 3, passes through the sample loop 38, reenters the valve 36 through port 8 and exits again through port 9. Thus, a slug of the oil having a volume corresponding to the internal volume of the sample loop (e.g., 55 microliters) is introduced into the carrier solution conduit 44. As this slug of oil and the carrier solution stream passes through the carrier solution conduit 44, they are mixed together and the color indicating reagent reacts with the free fatty acids in the oil and produces a color change which can be measured by the detector 50.

Preheating the oil sample and carrier solution streams to a temperature above a level where the oil components tend to separate by the preheating coils 32 and 34 and maintaining the diffusion coil 46 at about the same temperature provides a mixture of the oil and carrier solution for passage through the detector 50. This desired mixing is enhanced by the diffusion coil 46 which imparts radial mixing.

As mentioned above, the solvent used in the carrier solution should be miscible with substantially all the components of the oil, particularly the free fatty acids which usually are long chain fatty acids such as oleic acid. This ensures a more complete reaction between the fatty acids and the color indicating reagent and, therefore, a more accurate measurement by the detector. The solvent should be substantially colorless, should not absorb light in the wave length of the free fatty acids being analyzed, and should have either weak acid or weak base properties so that it does not act as an acid or base with respect to the color indicating reagent or the free fatty acids and interfer with the indicator reaction. In this regard, the solvent should have a "pka" close to that for the color indicating reagent and the free fatty acids. It also should have a relatively high boiling point so it does not volatize when heated during passage through the various heating coils and a relatively low freezing point so that it does not solidify at lower ambient temperatures in colder climates. For example, t-butanol generally is undesirable because it tends to solidify at relatively high ambient temperatures.

At present, n-butanol is the preferred solvent. Other alcohols, polyols and chlorinated hydrocarbons containing 3 to 8 carbon atoms can be used.

When ambient air is used to pressurize the carrier solution, moisture in the air is introduced into the system. For many carrier solutions, the addition of water up to a certain point affects the pH at which the color indicating agent changes color with a resulting effect on the accuracy of the measurement made by a colorimetric detector. This potential problem is minimized by adding sufficient water to the carrier solution to raise the water content to a level where additional water does not affect the pH. This level can be determined empirically with a calibrated colorimeter. For methyl red/n-butanol solutions, this level is approximately 5 milliliters of water per liter of solution.

The pH of commercially available organic solvents tends to vary from batch to batch and, consequently, the point at which the color indicating reagent changes color also can vary. To obviate possible batch-to-batch variations in the solvent pH, the solution is "neutralized" to a predetermined pH prior to adding the color indicating reagent. This can be accomplished by taking an aliquot of solvent (95% butanol/5% water, adding an equal aliquot of neutralized phenolpthalein/ethanol indicator solution and manually titrating with either 0.1N NaOH or 0.1 NHCl to permanent faint pink color of phenolpthaiein at 65° C. Based upon this determination, the pH of the solvent batch can then be adjusted upward or downward by adding a calculated amount of base or acid. After the solvent has been thus "neutralized", a sufficient amount of the color indicating reagent is added. The solvent is then additionally pH-adjusted to the optimum absorbance unit full scale (AUFS). As a guide, 0.4–0.5 AUFS (measured at 520 nm) is optimum for a methyl red/n-butanol/water carrier solution.

As used herein in connection with the solvent, the terms "pH" and "pka" mean a representation of the acidity or alkalinity of a reagent in an organic solvent and are not identical to the pH or pka of that reagent in an aquous system.

As mentioned above, the color indicating reagent must be capable of reacting with the free fatty acids in the oil and producing a measurable color change, the intensity of which indicates a concentration of free fatty acids. The chemical reaction between the free fatty acids and the color indicating reagent can be represented as follows:

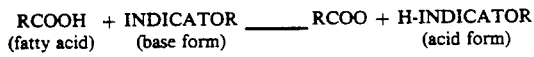

RCOOH + INDICATOR ⎯⎯⎯ RCOO + H-INDICATOR
(fatty acid)  (base form)             (acid form)

Thus, the color indicating reagent acts as a base which reacts with fatty acids as well as a color indicator. The color indicating reagent should have a "pKa" in the range of but slightly higher than that for the free fatty acids so there is a stoichiometric reaction between the free fatty acids and the color indicating reagent. For that reason, the carrier solution must contain at least a stoichiometric amount of the color indicating reagent.

At present, methyl red is the preferred color indicating reagent. Other suitable color indicating reagents include neutral red and azolitmin.

The presence of gas bubbles in the system can adversely affect the accuracy of the measurements made by the detector. The carrier solution reservoir usually is pressurized to about 25 psig and, if fully exposed to the pressurizing gas, the carrier solution would absorb a considerable amount of gas within a few hours. To minimize potential outgassing by gas absorbed into the carrier solution, the carrier solution reservoir is provided with means for substantially isolating the pressurizing gas from the carrier solution or, stated another way, for minimizing the effective surface area of the carrier solution exposed to the pressurizing gas.

In the preferred embodiment illustrated, discrete, bubble-like objects or hollow spheres 60 are floated on the surface of the carrier solution for this purpose. The spheres 60 are made from a material which is substantially inert with respect to the carrier solution. Two or more layers of the spheres 60 provide better isolation and, therefore, are preferred. As a guide, it has been found that three layers of ¾-inch, hollow polypropylene spheres about 1½ to 2 inches deep provides satisfactory protection against significant absorption of air by the carrier solution.

A quick-disconnect type filler connection 62 can be used on the carrier solution reservoir 20 so that carrier solution can be added to the reservoir without introducing significant amounts of air.

To further minimize outgassing, the system is designed so that there is a minimum pressure drop between the carrier solution reservoir 20 and the detector 50 under operating flow conditions. As a guide, the flow rate of the carrier solution stream usually is on the order of 1.5 to 2.0 ml/min, the inside diameter of the preheater coils 32 and 34, the sample loop 38 and the diffusion coil 46 is 0.030 inch, and the cross sectional areas of the flow passages of the slider valve 36 and connections between components in the system between the carrier solution reservoir 20 and the detector 50 are at least as large.

By minimizing the pressure drop in the system between the carrier solution reservoir and the detector, the flow rate of the carrier solution stream is governed by the pressure drop through the flow restrictor coil 58. The use of relatively long, coiled tubing (e.g., 3 meters) to provide the pressure drop required to obtain the desired flow rate permits the use of a cross sectional flow area (e.g., 0.02 inch inside diameter) which is large enough to prevent plugging by particulate matter in the oil. A single plate orifice small enough to provide the required pressure drop is subject to becoming plugged by such particulate matter. Maintaining the restrictor coil at a substantially constant temperature minimizes variations in flow due to changes in ambient temperature.

The calibration of the detector 50 tends to change because of changes in ambient temperature, normal instrumentation drift, etc. The system includes means for introducing a plurality of calibration solutions (e.g., up to 3) at programmable intervals and generating an updated calibration curve for the detector 50. The illustrated preferred embodiment includes a selector valve manifold 70 including the sample valve 17 and three separate calibration solution reservoirs 72, 74 and 76 pressurized to about 5 psig and connected to the sample conduit 14 via respective calibration conduits 78, 80 and 82. Each calibration conduit has a two-way, pneumatically-operated valve 84 which is selectively opened to introduce the corresponding calibration solution into the sample supply conduit 14.

Each calibration solution contains a known concentration of a free fatty acid, such as oleic acid, dissolved in an organic solvent, preferably the solvent as the one for the carrier solution. The organic solvent is "neutralized" as described above before adding the free fatty acid. As a guide, the free fatty acid concentration for the three different calibration solutions can be 0.015, 0.030 and 0.05 weight %.

When the system is in the calibrating mode, the sample valve 17 is closed and one valve 84 is opened with the slider valve 36 in the load position. After the sample loop 38 is filled with a first calibration solution, the slider valve 36 is moved to the measure position and a slug of the calibration solution is mixed with the carrier solution and passes through the detector 50 as described above. The selector valve 36 is returned to the load position, another valve 84 is opened to fill the sample loop 38 with a second calibration solution and the above cycle repeated for the second and third calibration solutions.

After the last calibration has been completed, the sample valve 17 is reopened. The sample waste conduit 40 preferably has no flow restrictions so that the sample supply conduit 14, the preheating coil 32 and the selector valve 36 can be rapidly flushed out before, between and after calibrations.

Figure 3:
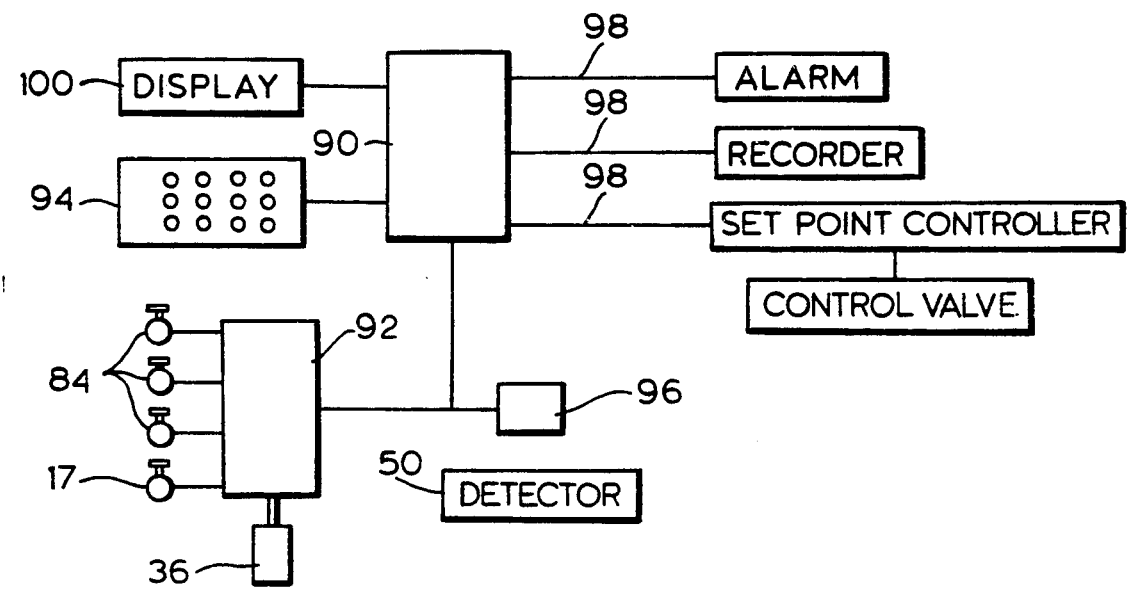
FIG. 3 is a diagrammatic representation of an automatic control for the system.

FIG. 3 is a diagrammatic representation of an automatic control for the system. Operation of the slider valve 36, the sample valve 17 and the calibration solution valves 84 is controlled by the central processing unit (CPU) 90 of a microprocessor (e.g., a Z80 microprocessor marketed by Zylog) which transmits signals to a valve driver board 92 connected to those valves. The valve driver board 92, through on/off switches, controls the pilot valves which pneumatically operate the slider valve 36, the sample valve 17 and the calibration valves 84.

The CPU 90 includes a real time computer program which initiates electrical signals for moving the slider valve 36 between the load and measure positions and for opening and closing the sample valve 17 and the calibrations solution valves 84. The time intervals for sampling and calibration are programmable and can be changed by inputting the appropriate data with a key pad 94 connected to the CPU 90. The output signal of the detector 50 is sent to a signal processing and analog/digital converter (A/D) board 96. The A/D board 96 converts the analog signals from the detector 50 to digitized signals which are transmitted to the CPU 90.

The CPU 90 contains a computer program which reads the signals from the signal processing and A/D board 96 and initiates electrical signals (represented by arrows 98) which can be used to trigger an alarm, drive a recorder and/or serve as an input to an automated process control system including a set point controller which operates a control valve. A vacuum fluorescent display 100 provides a visual readout of the current operating conditions or program parameters. The CPU 90 contains a computer program which reads the signals from the A/D board 96 during the calibration mode and stores an updated calibration curve for the detector 50. This calibration curve becomes the standard to which signals from the detector 50 during the measure mode are compared to produce the output signals 98.

From the foregoing description, one skilled in the art can easily ascertain the essential characteristics of the invention, and without departing from the spirit and scope thereof, make various changes and modifications to adapt it to various usages.

We claim:

1. An automated apparatus for determining free fatty acid content of an organic sample dissolved in a carrier solution comprising:
   i) a carrier solution supply means and carrier solution conduit providing a continuous stream of the carrier solution containing an indicating reagent capable of reacting with the free fatty acid of the sample wherein the carrier solution supply means comprises a solution reservoir means for pressuring the carrier solution in the reservoir to a predetermined pressure with an oxygen-free gas connected to the carrier solution supply conduit and means for substantially isolating the pressuring gas from the carrier solution;
   ii) a sample supply means and sample supply conduit;
   iii) sample injection valve connected to the sample supply conduit and carrier solution supply means wherein the sample injection valve is positionable between a load position having the carrier solution supply means connected to the carrier solution conduit and a sample collection conduit means connected between a sample waste collection means and the sample supply conduit and a measure position having the sample collection conduit connected between the carrier solution supply means and the carrier conduit means wherein the sample is contacted with the carrier solution;
   iv) the sample collection conduit including a sample loop with two ends and the two ends being connected to the sample injection valve;
   v) the sample waste collecting means in linear relationship to the sample supply means and connected to the sample injection valve;
   vi) a carrier waste collecting means connected to a detector;
   vii) a flow through detector effective to produce a signal representative of the free fatty acid content of the sample in response to the reaction of an indicating reagent with the free fatty acid content of the sample having an inlet connected to the carrier solution conduit and an outlet connected to the carrier waste means; and
   viii) means for regulating flow of the carrier solution through the detector.

2. An apparatus according to claim 1 further comprising control means for operating the sample injection valve and moving the valve between the load and measure positions at selected programmable intervals.

3. An apparatus according to claim 1 wherein the flow regulating means comprises:
   a flow restriction coil comprising a length of coiled tubing of reduced diameter connected to the carrier waste collecting means downstream of the detector outlet; and
   means for maintaining the temperature of the flow restrictor coil at a predetermined, substantially constant temperature.

4. A apparatus according to claim 3 wherein the temperature maintaining means comprises:
   preheating means located adjacent to and in fluid communication with an inlet of said sample injection valve for separately heating the sample and the carrier solution to a temperature above a level where components of the sample tend to separate.

5. A apparatus according to claim 1 further comprising a heatable diffuser coil for mixing the sample and carrier solution comprising a length of coiled tubing in the carrier solution conduit connected between the sample injection valve and the detector inlet.

6. An apparatus according to claim 1 wherein the isolating means in the carrier solution reservoir comprises one or more layers of a discrete, substantially inert, bubble-like material that floats on the surface of the carrier solution in the reservoir.

7. An apparatus according to claim 1 wherein the sample supply means comprises:
   a sample supply valve for selectively connecting the sample supply conduit with a source of the sample;
   at least one source of a calibration solution;
   at least one control calibration valve for selectively admitting a calibration solution into the sample supply conduit; and means for selectively opening and closing the sample valve and the calibration valve at programmable intervals and generating an updated calibration curve for the detector as the carrier solution flows therethrough.

8. An apparatus according to claim 1 further comprising a preheating coil comprising at least two lengths of coiled tubing connected to both the sample supply conduit and to the carrier solution conduit and means for heating each of the preheating coils to a predetermined temperature.

9. An apparatus according to claim 1 wherein the sample supply conduit and the carrier supply conduit and the flow restrictor coil are appropriately dimensioned so that there is a minimum pressure adjacent to and in fluid communication with an inlet end of the flow restrictor coil.

10. A method for determining the free fatty acid content of a continuous stream of a sample stream dissolved in a carrier solution stream comprising the steps of:
 (a) heating both the sample and carrier solution streams to suitable temperature;
 (b) mixing a predetermined volume of the sample stream with a continuous stream of the carrier solution containing a suitable solvent and a color indicating reagent;
 (c) reacting the free fatty acid in the combined streams with the color indicating reagent to give a reacted solution to produce a detectable signal representative of the free fatty acid content;
 (d) passing the reacted solution through a detector which produces a signal representative of fatty acid content of the sample; and
 (e) repeating steps (b)–(e) to determine the free fatty acid content of the sample at timed intervals.

11. A method according to claim 10 further comprising the steps of:
 (g) mixing a number of calibration solutions containing various quantities of a known free fatty acid concentration producing a signal representative of the known fatty acid;
 (h) producing a signal representative of the known fatty acid content of the calibration solutions;
 (i) detecting the signals to obtain a calibration curve for the detector.

12. A method according to claim 10 further comprising the step of regulating flow through the detector with a flow resistor coil downstream of the detector.

13. A method according to claim 10 further comprising the steps of:
 pressuring the carrier solution in a reservoir to a predetermined pressure with a gas and floating one or more layers of a discrete, substantially inert, bubble-like material on the surface of the carrier solution to minimize absorption of the gas into the carrier solution.

14. A method according to claim 10 wherein the color indicating reagent has a pKa value higher than the pKa value of the free fatty acid present in the sample and wherein the color indicating reagent reacts substantially stoichiometrically with the free fatty acid present in the sample.

15. A method according to claim 10 further comprising the step of adding sufficient water to the carrier solution to adjust the pH thereof to a point where additional added water does not substantially affect the pH value of the solution.

16. A method according to claim 10 wherein the pH of the carrier solution is adjusted to produce a predetermined full scale absorption unit for the color indicating reagent.

17. The method according to claim 10 wherein the sample is an edible oil and the carrier solution comprises methyl red and n-butanol.

* * * * *